United States Patent [19]

Simon et al.

[11] Patent Number: 5,061,476

[45] Date of Patent: Oct. 29, 1991

[54] RADIOLABELED COLLOID COMPOSITIONS AND METHOD FOR PREPARING SAME

[75] Inventors: Jaime Simon, Angleton; Lance A. Cooper, Lake Jackson; Kenneth McMillan; David A. Wilson, both of Richwood, all of Tex.

[73] Assignee: The Dow Chemical Company, Midland, Mich.

[21] Appl. No.: 458,049

[22] Filed: Dec. 27, 1989

[51] Int. Cl.$^5$ .................. A61K 43/00; A61N 5/12
[52] U.S. Cl. ........................ 424/1.1; 534/10; 534/11; 600/3; 600/4; 252/635
[58] Field of Search .................. 424/1.1; 600/3, 4; 534/10, 11

[56] References Cited

U.S. PATENT DOCUMENTS

| | | |
|---|---|---|
| 4,752,464 | 6/1988 | Lieberman et al. .................. 424/1.1 |
| 4,758,429 | 7/1988 | Gordon et al. ........................ 424/85 |
| 4,849,209 | 7/1989 | Lieberman et al. .................. 424/1.1 |
| 4,889,707 | 12/1989 | Day et al. ............................. 424/1.1 |
| 4,897,254 | 1/1990 | Simon et al. ......................... 424/1.1 |
| 4,898,724 | 2/1990 | Simon et al. ......................... 424/1.1 |
| 4,906,450 | 3/1990 | Lieberman et al. .................. 424/1.1 |
| 4,915,932 | 4/1990 | McLaren et al. ..................... 424/1.1 |
| 4,970,062 | 11/1990 | Atcher et al. ........................ 424/1.1 |

OTHER PUBLICATIONS

Handbook of Chemistry and Physics, 55th Edition, "Table of Isotopes", p. B-267-B-297 (CRC Press), 1974-1975.
Sledge et al., *Arthritis and Rheumatism*, vol. 20, No. 7, 1977, pp. 1334-1342.
Hnatowich et al., *J. Nucl. Med.*, vol. 19, No. 3, 1978, pp. 303-308.
Doepel, J. A. M. A., 253:744-745, 1985.
Rosenthall, In: *Therapy in Nuclear Medicine*, R. Spencer (Ed), Gruen & Stratton, New York, 1978, pp. 147-242.
Sledge et al., *Clinical Orthopedics and Related Research*, 182:37-40, 1984.
Sledge et al., *Arthritis and Rheumatism*, 29: 153-159, 1986.
Spooren et al., *Medicine*, In:*Springer-Verlag*, 1985, pp. 441-445.

*Primary Examiner*—Richard D. Lovering
*Assistant Examiner*—John M. Covert
*Attorney, Agent, or Firm*—Duane C. Ulmer; Ronald G. Brookens

[57] ABSTRACT

Radiolabeled colloid compositions and a method for the preparation of radionuclide-colloid compositions useful in the treatment of rheumatoid arthritis are disclosed. A radionuclide selected from the group consisting of Sm-135, Ho-166, In-155m, Y-90, Gd-159 La-140, Lu-177, or Yb-175 is sorbed to a previously prepared iron-hydroxide colloid. The radiolabeled colloid compositions are comprised of spherical aggregations containing greater than 50% of the radioactive metal in iron-hydroxide particles. The method produces stable radionuclide iron-hydroxide compositions which are useful in therapeutic procedures such as radiation synovectomy.

21 Claims, No Drawings

RADIOLABELED COLLOID COMPOSITIONS AND METHOD FOR PREPARING SAME

FIELD OF THE INVENTION

This invention relates to radiolabeled colloid compositions and to a method for producing radioactive colloid, wherein a radionuclide is sorbed to a previously prepared colloid. The radioactive colloid so produced is useful in the treatment of arthritis, especially rheumatoid arthritis.

BACKGROUND OF THE INVENTION

Rheumatoid arthritis is a prevalent disease characterized by chronic inflammation of the synovial membrane lining the afflicted joint. Current treatment methods for severe cases of rheumatoid arthritis include the removal of the synovial membrane, e.g., synovectomy. Surgical synovectomy has many limitations including the risk of the surgical procedure itself, and the fact that a surgeon often cannot remove all of the membrane. The diseased tissue remaining eventually regenerates, causing the same symptoms which the surgery was meant to alleviate.

Radiation synovectomy is radiation-induced ablation of diseased synovial membrane tissue accomplished by injecting a radioactive compound into the diseased synovium. Early attempts to perform radiation synovectomy were limited by leakage of the radioactive compounds from the synovium and into surrounding healthy tissues. Significant leakage of the radioactive compound from the injection site exposed normal tissues to dangerous levels of radiation. Because of these limitations, new radiolabelled colloids were sought which would be kinetically inert and of a sufficient size to restrict leakage.

The preparation of a radioactive colloid by a co-precipitation method is disclosed in U.S. Pat. No. 4,752,464. This method entraps a radionuclide in an iron hydroxide matrix. While compounds as described in U.S. Pat. No. 4,752,464 are useful for radiation synovectomy, their method of preparation is cumbersome in that it requires many chemical manipulations with highly radioactive compounds. The radioactive colloid particles produced by the coprecipitation method are of varied sizes and include sizes which will leak from the site of injection. Further, the radioactive compounds of choice are those with relatively short half-lives, consequently, radioactive colloids prepared by the coprecipitation method have an extremely limited shelf life, and the ability of a physician and patient to schedule therapeutic procedures is highly dependent upon prompt supply and delivery of the products.

Therefore, a method for producing radiolabeled colloids for use in the treatment of rheumatoid arthritis, which would be safe and easy to practice, which would produce colloid particles of a uniform size-distribution, and enable on-site addition of radionuclide and hence be cost-saving and more convenient for use by the daily practitioner is still needed. The present method addresses these needs.

SUMMARY OF THE INVENTION

A method for the preparation of a radiolabeled colloid is disclosed, wherein an iron-hydroxide (Fe(II) or Fe(III)) colloid is produced prior to the addition of radionuclide. This colloid may optionally be separated by size to remove fines and other small particles prior to the addition of radionuclide which would be likely to leak from the sight of injection during treatment and cause injury to normal tissues.

By the method of this invention, a prepared iron-hydroxide colloid may be stored or shipped for on-site radionuclide addition. Immediately prior to use, the appropriate radionuclide is sorbed onto the colloid to quickly prepare the radionuclide-iron hydroxide colloid for use in therapeutic procedures such as radiation synovectomy.

This sorption method of preparation minimizes the number of manipulations with radioactive compounds. The method also provides for the removal of undesirable fines and small particles which may leak from the site of injection. Further, this method provides for the preparation of a colloid which may be stored an indefinite period of time and shipped prior to the addition of radionuclides. The radioactive colloid may be quickly prepared by the physician just prior to therapeutic use.

The resulting product of this invention comprises a radionuclide sorbed onto an iron-hydroxide colloid, as opposed to a radionuclide being entrapped within the matrix of a colloid as in the products of the prior co-precipitation procedure. The radiolabeled colloid compositions of this invention are comprised of spherical aggregations of radioactive metal in iron-hydroxide particles. More specifically, the compositions of the present invention comprise iron-hydroxide and a radionuclide wherein greater than 50% of the radionuclide is contained within spherical aggregations of the iron hydroxide. In contrast, colloids prepared by the co-precipitation of iron and the radioactive metal are comprised of a homogeneous distribution of radioactive metal in needle-like crystals. Radiolabelled colloids prepared by the sorption method of this invention remain in the synovium as effectively or more effectively than similar entrapped radionuclide formulations prepared by the co-precipitation methods.

DETAILED DESCRIPTION OF THE PREFERRED EMBODIMENTS

An iron hydroxide colloid is prepared by the precipitation of an iron solution such as iron (II) or iron (III) sulfate with an alkali metal hydroxide, such as sodium hydroxide. The precipitate is washed in a suitable buffer at neutral pH, such as borate buffer, centrifuged and decanted to form a slurry.

If desired, the particles of the colloid slurry may be sized prior to the addition of radioactive metal. Particles greater than approximately 1-3 $\mu$m have generally been found to be of a sufficient size to be retained in the synovium of a joint. Particles of greater than 3 $\mu$m are preferred, and particles greater than 5 $\mu$m are more preferred. Such sizing may be accomplished by methods known in the art such as chromatographic separation, filtration, or differential centrifugation. The method employed may be optimized to remove particles of less than the desired size, or to more stringently separate out particles of a specific size range. A suitable radioactive metal may then be sorbed to the prepared colloid particles. Radioactive metals useful in radiation synovectomy include Sm-153; Ho-166; In-155m; Gd-159; La-140; Lu-177; Yb-175; and Y-90. The preferred radioactive metals are Sm-153, Ho-166, and In-155m. The therapeutically-effective amount of radionuclide to be added will vary according to the radionuclide used due to its half-life and emissions.

The respective radionuclides can be produced in several ways. In a nuclear reactor, a nuclide is bombarded with neutrons to obtain a nuclide with additional neutrons in its nucleus. For example:

Ho-165 + neutron → Ho-166 + gamma

Typically the desired radionuclide can be prepared by irradiating an appropriate target, such as the metal oxide. Another method of obtaining radionuclides is by bombarding nuclides with particles in a linear accelerator or cylclotron. Yet another way of obtaining radionuclides is to isolate them from fission product mixtures. The method of obtaining the radionuclide is not critical to this invention.

The term "sorption" includes both absorption and adsorption. In the method of this invention, a radionuclide is sorbed to the previously prepared iron-hydroxide colloid by mixing a radioactive metal with the colloid and then allowing the mixture to stand for a period of time ranging from 0-30 minutes, preferably 0.5-10 minutes. A preferred ratio of iron to radionuclide in the final colloid product is greater than 1.0 (mole:mole); a more preferred ratio is greater than 10.0 (mole:mole). The amount of activity of the radionuclide is dependent upon the particular radionuclide used. The preferred activity is that which is sufficient, when injected into the synovium of a subject, to completely ablate the synovial membrane, namely approximately 500 to 150,000 rads. A more preferred dose of radioactivity is that sufficient to deliver from about 2,000 to about 50,000 rads to the synovial membrane.

In one embodiment of this invention, fines, or very small particles are removed from the iron-hydroxide colloid, prior to the step of radionuclide sorption.

The sorbed radioactive colloids comprise spherical aggregations distributed within the crystaline structure containing the major portion of the radioactive metal. From 50 to 100% of the radionuclide may be within the spherical aggregations, preferably greater than 70%.

The sorbed radioactive colloids of this invention are useful in therapeutic procedures such as radiation synovectony. In this procedure, a therapeutically effective dose of the sorbed radioactive colloid is injected into the synovium of a subject suffering from rheumatoid arthritis. The appropriate dose of the sorbed radioactive colloid will vary according to the particular radionuclide, its specific activity and half-life, and the ratio of radioactive metal to iron-hydroxide colloid. In general, the dose will be that sufficient to provide from approximately 500 to 150,000 rads to the synovial membrane. The subject may be any animal in need of such treatment preferably a mammal, and more preferably a human.

To test the kinetic stability or lability of the radionuclide-colloid, the radioactive colloid may be challenged with excess metal chelators, such as diethylenetriaminepentaacetic acid (DTPA). The failure of excess chelator to displace the radioactive metal from the colloid is evidence that the colloid is stable and inert, and thus suited for use in radiation synovectomy.

The invention will be further clarified by consideration of the following examples, which are intended to be purely exemplary of the method of the invention.

EXAMPLES

EXAMPLE 1

Preparation of Iron-Hydroxide Colloid

An iron (II) solution was prepared by the addition of 0.5 ml of 0.2% (0.2 g/100 ml) ferrous sulfate to 5 ml of deionized water. To this solution was added 2 ml of 1.0 M sodium hydroxide. The resulting precipitate was isolated by centrifugation, using a Model 2K centrifuge (International Equipment Co.) for 2.5 to 3 minutes at a speed setting of 45 on a scale from 0-50. The centrifuged pellet was washed first with 2 ml of water, and then with 2 ml of borate buffer, pH 7. The supernatant liquid was decanted to yield an iron hydroxide slurry.

EXAMPLE 2

Sorption of Sm-153 to the Iron-Hydroxide Colloid

To the 0.3 ml iron-hydroxide slurry prepared in Example 1 was added 30 $\mu$l of a Sm-153 solution in 0.1 N HCl ($3 \times 10^{-4}$M Sm), which resulted in a solution containing approximately 8,000 counts per minute. The amount of radiation was determined using a multichannel analyzer equipped with a NaI well detector. This was stirred and allowed to stand for approximately five minutes at room temperature, and then was filtered through a 0.45 micron filter. The relative amount of Sm-153 in the filter paper and in the wash was determined by counting the radioactivity as described above. The results indicated that greater than 99% of the Sm-153 was associated with the iron-hydroxide colloid.

EXAMPLE 3

Challenge of Sm-153-Iron-Hydroxide Colloid with DTPA

The filters containing the Sm-153-iron-hydroxide colloid prepared in Example 2 were challenged with excess chelator, DTPA, by flushing the filters with 0.3 ml of DTPA solution ($3.3 \times 10^{-4}$M, pH 7.5). The relative amount of radioactivity in the filter and in the wash was then determined. The results indicated that less than 0.2% of the Sm-153 was displaced from the iron-hydroxide colloid by the excess chelant treatment.

EXAMPLE 4

Injection of Sm-153-Iron-Hydroxide Colloid into Rabbit Synovium

The Sm-153-iron hydroxide colloid prepared in Example 2 was injected (100 $\mu$l) into the synovium of the stifle of the hind leg of a rabbit. Counts of the knee area were taken using a NaI scintillation detector over a four hour period. Greater than 99% of the injected dose of radioactivity remained in the synovium, with no leakage into surrounding tissues during this 4 hour period.

EXAMPLE 5

Preparation of Ho-166-Iron-Hydroxide Colloid

The procedure of Example 2 was followed using the radioactive compound Ho-166 to prepare the radioactive colloid. The results indicated that greater than 99% of the Ho-166 was associated with the iron-hydroxide colloid.

EXAMPLE 6

Challenge of Ho-166-Iron-Hydroxide Colloid with DTPA

The Ho-166-iron hydroxide colloid prepared in Example 5 was challenged with DTPA as described in Example 3. The results less than 0.2% of the Ho-166 was displaced from the colloid by the addition of the excess chelator.

EXAMPLE 7

Injection of Ho-166-Iron-Hydroxide Colloid into Rabbit Synovium

The Ho-166-iron hydroxide colloid prepared in Example 5 was injected (100 μl) into the synovium of the stifle of the hind leg of a rabbit. Ho-166-iron-hydroxide colloid was also prepared according to the method of Hnatowich et. al., following the procedure described on page 305 of this article. This colloid was also injected (100 μl) into the synovium of the stifle of the hind leg of a rabbit.

As in Example 4, counts of the knee areas over a four hour period were taken. Results for the sorbed-radioactive colloid indicated that greater than 99% of the radioactivity remained in the synovium, with no leakage into surrounding tissues. In contrast, results for the colloid prepared by an "entrapment" co-precipitation method indicated only 95% of the activity remained in the synovium after 4 hours of treatment.

EXAMPLE 8

Comparison of Physical Characteristics of Sorbed-Holmium Colloid Versus Co-precipitated Holmium Colloid.

Samples of Ho-iron-hydroxide colloid were prepared according to the sorption method in Example 5 using only non-radioactive Ho-165. Ho-iron-hydroxide colloid was also prepared by the co-precipitation method in Example 7 using only non-radioactive Ho-165. The non-radioactive Ho-iron-hydroxide preparations were viewed in a transmission electron microscope. The colloid prepared by each method was readily distinguishable by the distribution of the Ho metal. Holmium (Ho) was distributed in a homogenous manner throughout the needle-like crystals of the colloid prepared by the co-precipitation method. In contrast, the new composition prepared by sorption of the holmium onto the previously prepared iron hydroxide was comprised of spherical aggregates of iron-hydroxide which contained the majority of the holmium metal (approximately 80-90%).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for producing a radioactive composition, comprising the steps of:
   (a) preparing an iron-hydroxide colloid by precipitating an iron solution with an alkali metal hydroxide; and
   (b) sorbing onto the iron-hydroxide colloid a radionuclide selected from the group consisting of Sm-153, Ho-166, In-115m, Y-90, Gd-159, La-140, Lu-177 and Yb-175.

2. The method of claim 1, wherein the iron solution of step (a) is a solution comprising iron (II).

3. The method of claim 1, wherein the iron solution of step (a) is a solution comprising iron (III).

4. The method of claim 1, wherein the radionuclide of step (b) is selected from the group consisting of Sm-153, Ho-166 and In-115m.

5. The method of claim 1, wherein said sorbing is accomplished by preparing a mixture of a radionuclide with the iron-hydroxide colloid wherein the mixture is further permitted to stand for a period of up to 30 minutes.

6. The method of claim 1, including the additional step of filtering the iron-hydroxide colloid formed in step (a) prior to step (b).

7. A composition comprising iron-hydroxide and a radionuclide selected from the group consisting of Sm-153, Ho-166, In-115m, Y-90, Gd-159, La-140, Lu-177 and Yb-175, wherein greater than 50% of the radionuclide is contained within spherical aggregations of the iron hydroxide, and wherein particles of the composition are of a size sufficient to prevent significant leakage from a site of injection.

8. The composition of claim 7, wherein said spherical aggregations contain greater than 70% of the radionuclide.

9. The composition of claim 7, wherein the iron-hydroxide is iron (II)-hydroxide.

10. The composition of claim 7, wherein the iron-hydroxide is iron (III)-hydroxide.

11. The composition of claim 7, wherein the radionuclide is selected from the group consisting of Sm-153, Ho-166, and In-115m.

12. A method for the treatment of arthritis comprising sorbing a radionuclide selected from the group consisting of Sm-153, Ho-166, In-115m, Y-90, Gd-159, La-140, Ju-175 and Yb-175 onto a previously prepared iron-hydroxide colloid; and injecting into the synovium of a subject in need of such treatment a therapeutically effective amount of the composition thus formed.

13. A method for the treatment of arthritis comprising injecting into the synovium of a subject in need of such treatment a therapeutically effective amount of a composition comprising iron-hydroxide and a radionuclide selected from the group consisting of Sm-153, Ho-166, In-115m, Y-90, Gd-159, the radionuclide is contained within spherical aggregations of the iron-hydroxide.

14. The method of claim 13, wherein said spherical aggregations contain greater than 70% of the radionuclide.

15. The method of claim 13, wherein the iron hydroxide is iron (II) hydroxide.

16. The method of claim 13, wherein the iron hydroxide is iron (III) hydroxide.

17. The method of claim 13, wherein the radionuclide is selected from the group consisting of Sm-153, Ho-166 and In-115m.

18. The method of claim 13, wherein said arthritis is rheumatoid arthritis.

19. The method of claim 13, wherein said injecting is to the synovium of a joint of the subject.

20. The method of claim 13, wherein said subject is a mammal.

21. The method of claim 20, wherein said mammal is a human.

* * * * *